US010568660B2

(12) United States Patent
Zhou

(10) Patent No.: US 10,568,660 B2
(45) Date of Patent: Feb. 25, 2020

(54) RADIAL SEALING ASSEMBLY, END SEALING PIECE AND TROCAR

(71) Applicant: Guangzhou T.K Medical Instrument Co., Ltd., Guangzhou (CN)

(72) Inventor: Xing Zhou, Guangzhou (CN)

(73) Assignee: GUANGZHOU T.K MEDICAL INSTRUMENT CO., LTD., Guangzhou (CN)

( * ) Notice: Subject to any disclaimer, the term of this patent is extended or adjusted under 35 U.S.C. 154(b) by 257 days.

(21) Appl. No.: 15/595,728

(22) Filed: May 15, 2017

(65) Prior Publication Data

US 2017/0265895 A1    Sep. 21, 2017

Related U.S. Application Data

(63) Continuation of application No. PCT/CN2015/093709, filed on Nov. 3, 2015.

(30) Foreign Application Priority Data

Nov. 16, 2014    (CN) .......................... 2014 1 0655716

(51) Int. Cl.
*A61B 17/34*    (2006.01)
*A61M 39/06*    (2006.01)
*A61M 39/02*    (2006.01)

(52) U.S. Cl.
CPC .......... *A61B 17/3462* (2013.01); *A61B 17/34* (2013.01); *A61M 39/06* (2013.01);
(Continued)

(58) Field of Classification Search
CPC ............ A61B 17/3462; A61B 17/3498; A61B 2017/3464; A61B 2017/3466;
(Continued)

(56) References Cited

U.S. PATENT DOCUMENTS 5,342,315 A * 8/1994 Rowe ................. A61B 17/3462
604/167.06
5,968,060 A * 10/1999 Kellogg ......... A61B 17/320068
606/169

(Continued)

FOREIGN PATENT DOCUMENTS

CN    203710094    *    7/2014    ......... A61B 17/3462
JP    2005-103285 A        4/2005
(Continued)

OTHER PUBLICATIONS

Gruangzhou T.K. Medical Instrument Co., Ltd., Office Action, JP2017-526546, dated Sep. 20, 2018, 4 pgs.
(Continued)

*Primary Examiner* — Lauren P Farrar
*Assistant Examiner* — James D Ponton
(74) *Attorney, Agent, or Firm* — Morgan, Lewis & Bockius LLP

(57) ABSTRACT

A radial sealing assembly comprises an upper pressing plate, a protection sheet, a positioning plate, a funnel-shaped sealing ring, a lower pressing plate and a corrugated sealing ring. The upper pressing plate is provided with at least two convex connecting hooks for connection with the positioning plate; the lower pressing plate is provided with at least two connecting slots for connection with the positioning plate; the positioning plate is provided with at least two connecting slots for connection with the upper pressing plate and at least two convex connecting hooks for connection with the lower pressing plate; and both the upper pressing plate and the lower pressing plate are connected to the positioning plate by adopting concave-convex engagement structures.

8 Claims, 10 Drawing Sheets

(52) U.S. Cl.
CPC ...... *A61B 2017/3464* (2013.01); *A61M 39/02* (2013.01); *A61M 2039/0626* (2013.01)

(58) Field of Classification Search
CPC .............. A61M 39/06; A61M 39/0606; A61M 39/0613; A61M 2039/0626
See application file for complete search history.

(56) References Cited

U.S. PATENT DOCUMENTS

| | | |
|---|---|---|
| 2005/0171479 A1 | 8/2005 | Kruska et al. |
| 2007/0185453 A1 | 8/2007 | Michael et al. |
| 2007/0255218 A1* | 11/2007 | Franer ................ A61B 17/3462 604/167.02 |
| 2008/0249475 A1* | 10/2008 | Albrecht ............ A61B 17/3498 604/167.06 |
| 2010/0217087 A1 | 8/2010 | Bonadio et al. |
| 2014/0171744 A1 | 6/2014 | Racenet et al. |

FOREIGN PATENT DOCUMENTS

| | | |
|---|---|---|
| JP | 2005-288174 A | 10/2005 |
| JP | 2010-148896 A | 7/2010 |
| WO | WO2012/131746 | 10/2012 |

OTHER PUBLICATIONS

Gruangzhou T.K. Medical Instrument Co., Ltd., Office Action, KR2017-7015888, dated Jun. 19, 2017, 4 pgs.
Gruangzhou T.K. Medical Instrument Co., Ltd., Office Action, KR2017-7015888, dated Jan. 18, 2019, 6 pgs.
Zhou, Communication Pursuant to Rules 162(2) and 162, EP15859620.5, Jul. 4, 2017, 2 pgs.
Zhou, Communication Pursuant to Rules 70(2) and 70A(2), EP15859620.5, Jun. 12, 2018, 1 pg.
Zhou Extended European Search Report, EP15859620.5, dated May 24, 2018, 6 pgs.

* cited by examiner

RADIAL SEALING ASSEMBLY, END SEALING PIECE AND TROCAR

PRIORITY CLAIM AND RELATED APPLICATIONS

This application is a continuation application of PCT Patent Application No. PCT/CN2015/093709, entitled "RADIAL SEAL ASSEMBLY, END SEAL AND TROCAR" filed on Nov. 3, 2015, which claims priority to Chinese Patent Application No. 201410655716.5, entitled "RADIAL SEALING ASSEMBLY, END SEALING PIECE AND TROCAR" filed on Nov. 16, 2014, both of which are incorporated by reference in their entirety.

TECHNICAL FIELD

The present application relates to a laparoscopic surgical instrument, and in particular to a radial sealing assembly, end sealing piece and trocar used in laparoscopic surgeries.

BACKGROUND OF THE INVENTION

Laparoscopic surgeries are applied more and more widely. In order to prevent iatrogenic infections, the usage of disposable trocars used in laparoscopic surgeries becomes larger and larger. The trend of simplifying structures, the trend of reducing costs and improving performance on the basis of ensuring operational performance has become the direction of trocar improvement.

A radial sealing assembly of the prior art normally comprises an upper pressing plate, a protection sheet, a positioning plate, a funnel-shaped sealing ring, a lower pressing plate and a corrugated sealing ring. After positioning pins of the upper pressing plate sequentially pass through mounting holes of the protection sheet and mounting holes of the corrugated sealing ring, the protection sheet and the corrugated sealing ring are mounted between the upper pressing plate and the positioning plate. After positioning pins of the lower pressing plate pass through mounting holes of the funnel-shaped sealing ring, the funnel-shaped sealing ring is fixed between the lower pressing plate and the positioning plate. By means of the interference fit between the positioning pins and the mounting holes, the upper pressing plate and the lower pressing plate are respectively fixedly connected to the positioning plate. Because the mounting edge of the corrugated sealing ring is compressed between the upper pressing plate and the positioning plate while the funnel-shaped sealing ring is compressed between the lower pressing plate and the positioning plate, under the elastic effect of the elastic material of the sealing rings, the upper pressing plate or the lower pressing plate can easily get loose from the positioning plate, which causes the radial sealing assembly to leak air, and as a result, the air tightness of an end sealing piece and an entire trocar is affected. Therefore, the radial sealing assembly, end sealing piece and trocar in the prior art need to be improved.

SUMMARY

A radial sealing assembly 12 of the present application comprises an upper pressing plate 12-1, a protection sheet 12-2, a positioning plate 12-3, a funnel-shaped sealing ring 12-4, a lower pressing plate 12-5 and a corrugated sealing ring 12-6; after positioning pins 121-1 of the upper pressing plate 12-1 sequentially pass through mounting holes 122-1 of the protection sheet 12-2 and mounting holes 126-1 of the corrugated sealing ring 12-6, the protection sheet 12-2 and the corrugated sealing ring 12-6 are mounted between the upper pressing plate 12-1 and the positioning plate 12-3; and after positioning pins 125-1 of the lower pressing plate 12-5 pass through mounting holes 124-1 of the funnel-shaped sealing ring 12-4, the funnel-shaped sealing ring 12-4 is fixed between the lower pressing plate 12-5 and the positioning plate 12-3; and the radial sealing assembly 12 is characterized in that:

A. The upper pressing plate 12-1 and the positioning plate 12-3 are connected together by adopting a concave-convex engagement structure; and B. The lower pressing plate 12-5 and the positioning plate 12-3 are connected together by adopting a concave-convex engagement structure.

Since the upper pressing plate 12-1 and the positioning plate 12-3 are connected together through the concave-convex engagement structure, even under the elastic effect of the elastic material of the corrugated sealing ring 12-6, the fixed connection between the upper pressing plate 12-1 and the positioning plate 12-3 can still be kept well without getting loose and leaking air. Likewise, since the lower pressing plate 12-5 and the positioning plate 12-3 are connected together through the concave-convex engagement structure, even under the elastic effect of the elastic material of the funnel-shaped sealing ring 12-4, the fixed connection between the lower pressing plate 12-5 and the positioning plate 12-3 can still be kept well without getting loose and leaking air.

In addition, the connection method of the concave-convex engagement structure is more convenient to assemble than connection methods such as interference fit, consequently, not only is the efficiency of production increased, but also connection is firmer, the connection mode is less easy to get loose and leak air, and thereby the sealing property of the radial sealing assembly 12 is better ensured. The assembling process of the concave-convex engagement method does not use chemical adhesive, errors in the process of operation cannot easily occur, and therefore it is safer. For example, if an adhesive connection method is chosen, the problem that connection is not firm due to uneven adhesive application can easily occur.

Further, the radial sealing assembly 12 also has the following characteristics:

A. The upper pressing plate 12-1 is provided with at least two convex connecting hooks 121-2 for connection with the positioning plate 12-3, and each convex connecting hook 121-2 is provided with a wedged guiding surface 1212-1 and a positioning working surface 1212-2;

B. The positioning plate 12-3 is provided with at least two connecting slots 123-1 for connection with the upper pressing plate 12-1 and at least two convex connecting hooks 123-2 for connection with the lower pressing plate 12-5; and each convex connecting hook 123-2 is provided with a guiding surface 1232-1 and a positioning working surface 1232-2;

C. The lower pressing plate 12-5 is provided with at least two connecting slots 125-2 for connection with the positioning plate 12-3; and D. The convex connecting hooks 121-2 of the upper pressing plate 12-1 are embedded in the connecting slots 123-1 of the positioning plate 12-3, so that a concave-convex engagement structure is formed to connect the upper pressing plate 12-1 and the positioning plate 12-3 together; and the convex connecting hooks 123-2 of the positioning plate 12-3 are embedded in the connecting slots 125-2 of the lower pressing plate 12-5, so that a concave-convex engagement structure is formed to connect the lower pressing plate 12-5 and the positioning plate 12-3 together.

Since at least two concave-convex engagement connections are arranged between both of the upper pressing plate 12-1 and the lower pressing plate 12-5 and the positioning plate 12-3, connection is firmer and more reliable.

Since the convex connecting hooks 121-2 of the upper pressing plate 12-1 are provided with the wedged guiding surfaces 1212-1, during mounting, the convex connecting hooks 121-2 can be conveniently embedded into the connecting slots 123-1 of the positioning plate 12-3. Since the convex connecting hooks 121-2 are also provided with the positioning working surfaces 1212-2, after the convex connecting hooks 121-2 are embedded into the connecting slots 123-1 of the positioning plate 12-3, the positioning working surfaces 1212-2 can play a good positioning role, effectively preventing the convex connecting hooks 121-2 from slipping out of the connecting slots 123-1 of the positioning plate 12-3, and thereby the firmness of connection is ensured.

Since the convex connecting hooks 123-2 for connection with the lower pressing plate 12-5 on the positioning plate 12-3 are provided with the guiding surfaces 1232-1, during mounting, the convex connecting hooks 123-2 of the positioning plate 12-3 can be conveniently embedded into the connecting slots 125-2 of the lower pressing plate 12-5, so that the concave-convex engagement structure is formed. Since the convex connecting hooks 123-2 for connection with the lower pressing plate 12-5 on the positioning plate 12-3 are also provided with the positioning working surfaces 1232-2, after the convex connecting hooks 123-2 are embedded into the connecting slots 125-2 of the lower pressing plate 12-5, the positioning working surfaces 1232-2 can effectively prevent the convex connecting hooks 123-2 from slipping out of the connecting slots 125-2 of the lower pressing plate 12-5, and thereby the firmness of connection is ensured.

Further, the upper pressing plate 12-1 is provided with four convex connecting hooks 121-2 for connection with the positioning plate 12-3; the positioning plate 12-3 is provided with four connecting slots 123-1 for connection with the upper pressing plate 12-1 and four convex connecting hooks 123-2 for connection with the lower pressing plate 12-5; and the lower pressing plate 12-5 is provided with four connecting slots 125-2 for connection with the positioning plate 12-3.

Such a four-hole positioning design can ensure the firmness of connection in all directions; on the other hand, the direction of mounting does not need to be deliberately chosen in the mounting process of the four-hole positioning design, and thereby the mounting of the radial sealing assembly 12 is facilitated.

Through holes 123-3 are arranged over the convex connecting hooks 123-2 of the positioning plate 12-3. The arrangement of the through holes 123-3 facilitates stripping, and also decreases surrounding force at the convex connecting hooks 123-2, and thereby the convex connecting hooks 123-2 can conveniently slide into the connecting slots 125-2 of the lower pressing plate to form convex-concave engagement during mounting.

Normally, the connecting slots 123-1 of the positioning plate 12-3 are arranged at the upper end of the inner side of the positioning plate 12-3, and the convex connecting hooks 123-2 of the positioning plate 12-3 are arranged at the lower end of the inner side of the positioning plate 12-3. During mounting, the connection between the upper pressing plate 12-1 and the positioning plate 12-3 is carried out through the connecting slots 123-1 of the upper part of the positioning plate 12-3; and the connection between the lower pressing plate 12-5 and the positioning plate 12-3 is carried out through the convex connecting hooks 123-2 of the lower part of the positioning plate 12-3. In the process of assembly, the assembly of the upper pressing plate 12-1 will not interfere with the assembly of the lower pressing plate 12-5, which facilitates the assembly of the radial sealing assembly 12.

The upper pressing plate 12-1 is provided with notches 121-3 which facilitate mounting. Since the notches 121-3 are arranged beside the convex connecting hooks 121-2 of the upper pressing plate 12-1, during assembly, the convex connecting hooks 121-2 can be moderately deformed, and thereby the convex connecting hooks 121-2 can conveniently slide and be embedded into the connecting slots 123-1 of the positioning plate to form concave-convex engagement fixation.

The present application also comprises an end sealing piece, and the end sealing piece 1 comprises the radial sealing assembly 12 of claim 1.

Further, the end sealing piece 1 is characterized in that:

A. The end sealing piece 1 comprises an upper cover 11, a pressing ring 13, a lower cover 14, and the radial sealing assembly 12 of claim 1;

B. The radial sealing assembly 12 and the pressing ring 13 are mounted in a space defined by the upper cover 11 and the lower cover 14; and the outer edge of the corrugated sealing ring 12-6 on the radial sealing assembly 12 is embedded between a sealing rib 14-1 of the lower cover 14 and the pressing ring 13, so that the corrugated sealing ring 12-6 is compressed by the upper cover 11; and C. The upper cover 11 and the lower cover 14 are connected together by welding or sticking or interference fit or through a concave-convex engagement structure.

Further, the upper cover 11 is provided with at least two convex connecting hooks 11-1; the lower cover 14 is provided with at least two connecting slots 14-2; and the convex connecting hooks 11-1 of the upper cover 11 are embedded in the connecting slots 14-2 of the lower cover 14, so that a concave-convex engagement structure is formed for fixed connection.

Since the upper cover 11 and the lower cover 14 adopt the concave-convex engagement connection method, mounting is convenient, moreover, the firmness of connection can be effectively ensured, and air leakage can be prevented.

Further, the upper cover 11 is provided with four convex connecting hooks 11-1; and the lower cover 14 is provided with four connecting slots 14-2. Such four concave-convex engagement connections formed by the four convex connecting hooks 11-1 and the four connecting slots 14-2 ensure the firmness of connection.

The present application also comprises a trocar, and the trocar comprises the radial sealing assembly 12 of claim 1.

The radial sealing assembly 12 of the present application comprises an upper pressing plate 12-1, a protection sheet 12-2, a positioning plate 12-3, a funnel-shaped sealing ring 12-4, a lower pressing plate 12-5 and a corrugated sealing ring 12-6. The upper pressing plate 12-1 is provided with at least two convex connecting hooks 121-2 for connection with the positioning plate 12-3; the lower pressing plate 12-5 is provided with at least two connecting slots 125-2 for connection with the positioning plate 12-3; the positioning plate 12-3 is provided with at least two connecting slots 123-1 for connection with the upper pressing plate 12-1 and at least two convex connecting hooks 123-2 for connection with the lower pressing plate 12-5; and both the upper pressing plate 12-1 and the lower pressing plate 12-5 are connected to the positioning plate 12-3 by adopting concave-convex engagement structures. Assembly is convenient, and the efficiency of production is high; moreover, the elasticity of sealing ring material can be effectively resisted, connection is firm, and air cannot leak out. Not only does the end sealing piece 1 of the present application comprise the radial sealing assembly 12 of the present application, but also the upper cover 11 and the lower cover 14 are connected together with a concave-convex engagement structure. The trocar of the present application comprises the radial sealing assembly 12 of the present application, and has the advantages of convenience in assembly, effective resistance against the elasticity of sealing ring material, firm connection and no air leakage.

BRIEF DESCRIPTION OF THE DRAWINGS

FIG. 5-1 is a top view of FIG. 5.

FIG. 5-2 is a B-B section view of FIG. 5-1.

FIG. 6-1 is a top view of FIG. 6.

FIG. 6-2 is a C-C section view of FIG. 6-1.

FIG. 7-1 is a top view of FIG. 7.

FIG. 7-2 is a D-D section view of FIG. 7-1.

FIG. 10-1 is a top view of FIG. 10.

FIG. 10-2 is an F-F section view of FIG. 10-1.

FIG. 11-1 is a top view of FIG. 11.

FIG. 11-2 is a G-G section view of FIG. 11-1.

FIG. 12-1 is a top view of FIG. 12.

FIG. 12-2 is an H-H section view of FIG. 12-1.

In the drawings:

100 is the trocar of the present application, 101 is a trocar rod of the trocar of the present application, and 102 is a sheath tube of the trocar of the present application.

1 is the end sealing piece of the present application, and 2 is a sleeve of the trocar of the present application.

11 is the upper cover, 12 is the radial sealing assembly, 13 is the pressing ring, and 14 is the lower cover.

11-1 is convex connecting hooks of the upper cover.

12-1 is the upper pressing plate, 12-2 is a protection sheet, 12-3 is the positioning plate, 12-4 is a funnel-shaped sealing ring, 12-5 is the lower pressing plate, and 12-6 is a corrugated sealing ring.

14-1 is a sealing rib of the lower cover, and 14-2 is connecting slots of the lower cover.

121-1 is positioning pins, 121-2 is convex connecting hooks for connection with the positioning plate on the upper pressing plate, and 121-3 is notches.

122-1 is mounting holes of the protection sheet.

123-1 is connecting slots for connection with the upper pressing plate in the positioning plate, 123-2 is convex connecting hooks for connection with the lower pressing plate on the positioning plate, and 123-3 is through holes.

124-1 is mounting holes of the funnel-shaped sealing ring.

125-1 is positioning pins of the lower pressing plate, and 125-2 is connecting slots for connection with the positioning plate in the lower pressing plate.

126-1 is mounting holes of the corrugated sealing ring.

1212-1 is wedged guiding surfaces of the convex connecting hooks for connection with the positioning plate on the upper pressing plate, and 1212-2 is positioning working surfaces of the convex connecting hooks for connection with the positioning plate on the upper pressing plate.

1232-1 is guiding surfaces of the convex connecting hooks for connection with the lower pressing plate on the positioning plate, and 1232-2 is positioning working surfaces of the convex connecting hooks for connection with the lower pressing plate on the positioning plate.

DESCRIPTION OF EMBODIMENTS

Embodiment 1: A Radial Sealing Assembly of the Present Application

The radial sealing assembly 12 of the present application comprises an upper pressing plate 12-1, a protection sheet 12-2, a positioning plate 12-3, a funnel-shaped sealing ring 12-4, a lower pressing plate 12-5 and a corrugated sealing ring 12-6, referring to FIG. 1 to FIG. 7-2.

Figure 1:
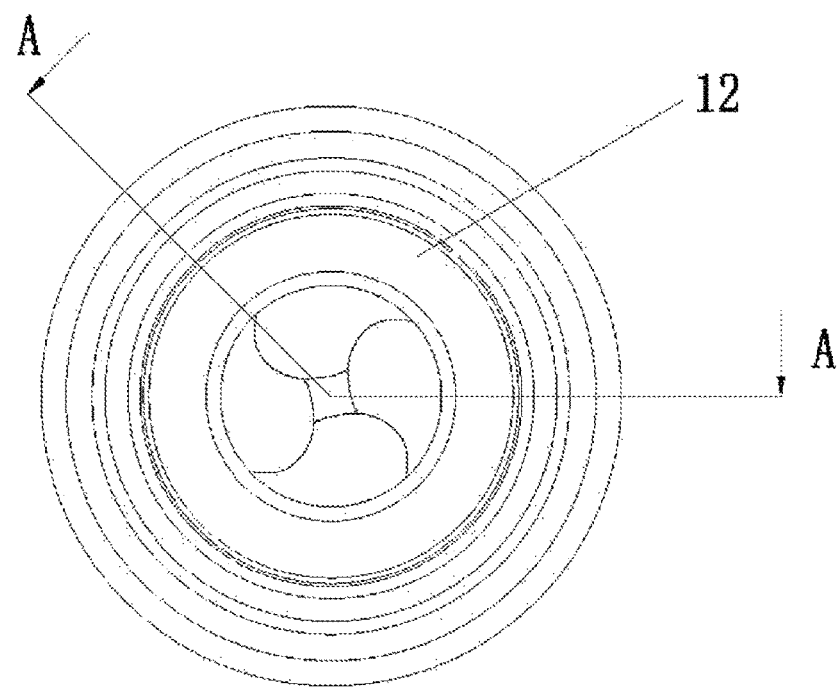
FIG. 1 is a structural schematic diagram of a radial sealing assembly of the present application.
Figure 2:
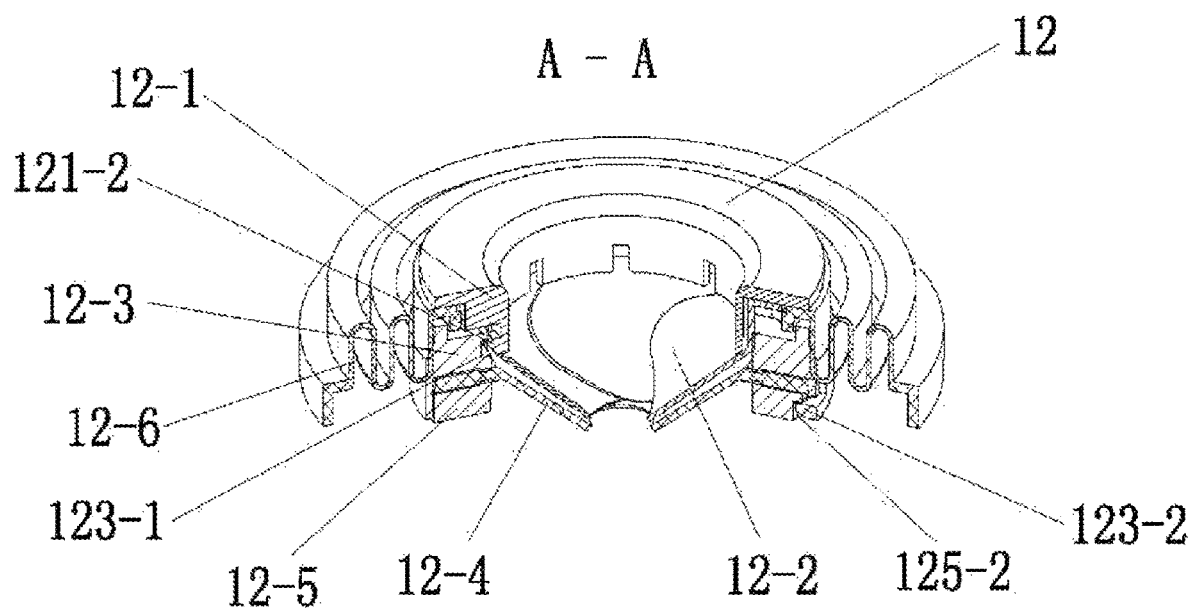
FIG. 2 is an A-A section view of FIG. 1.
Figure 3:
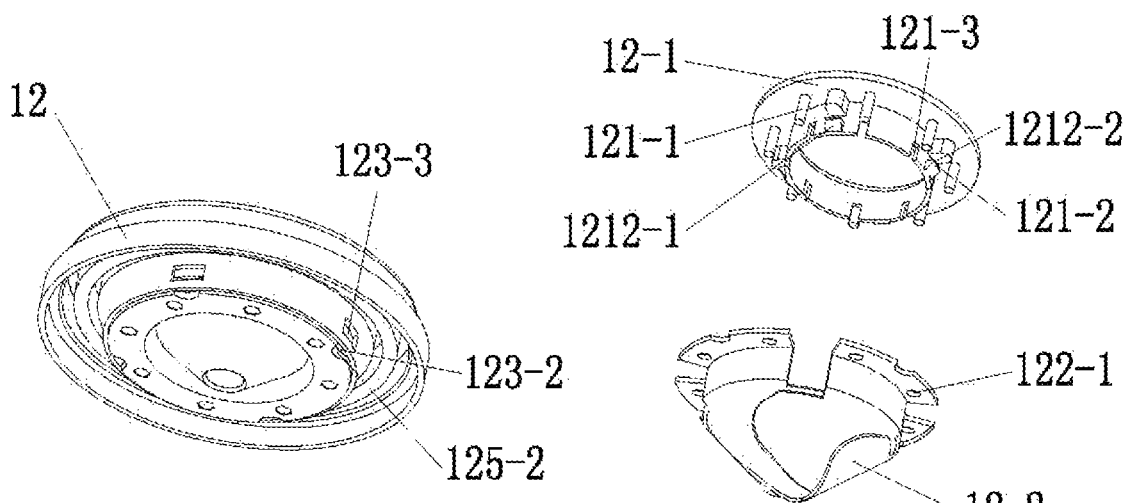
FIG. 3 is a stereostructural schematic diagram of the radial sealing assembly of the present application.
Figure 4:
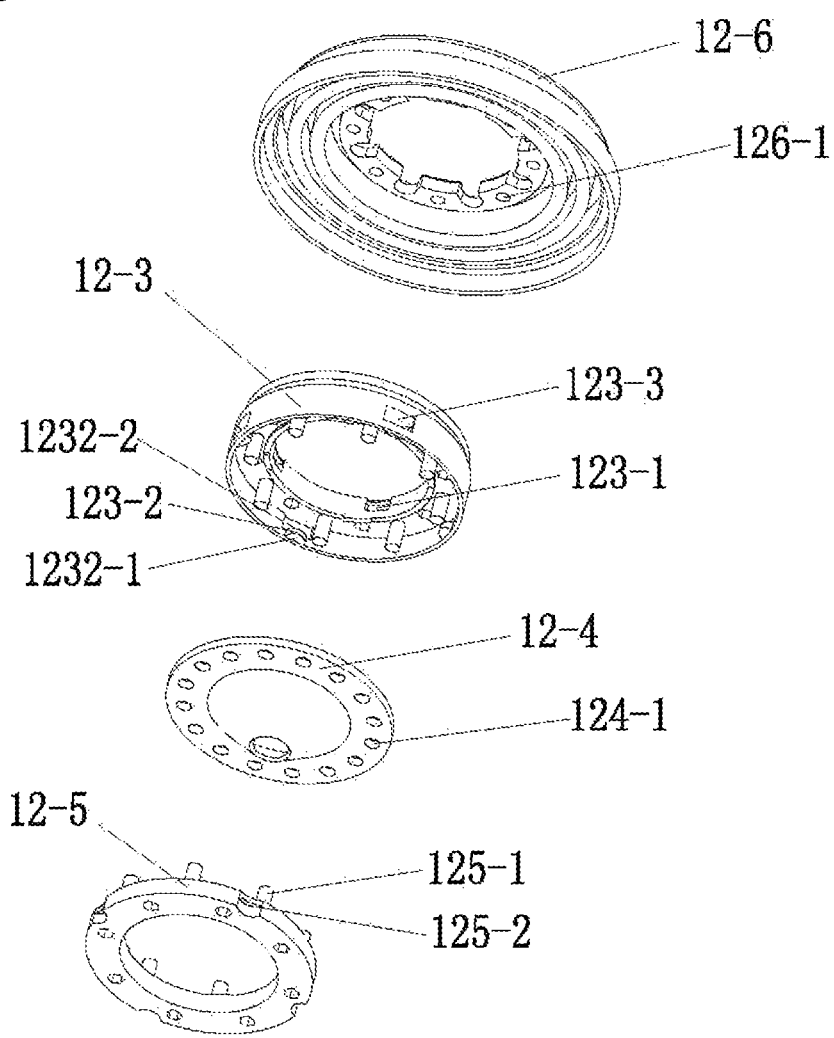
FIG. 4 is an exploded view of FIG. 3.

The upper pressing plate 12-1 and the positioning plate 12-3 are connected together by adopting a concave-convex engagement structure, referring to FIG. 2. The lower pressing plate 12-5 and the positioning plate 12-3 are connected together by adopting a concave-convex engagement structure, referring to FIG. 2. After positioning pins 121-1 of the upper pressing plate 12-1 sequentially pass through mounting holes 122-1 of the protection sheet 12-2 and mounting holes 126-1 of the corrugated sealing ring 12-6, the protection sheet 12-2 and the corrugated sealing ring 12-6 are mounted between the upper pressing plate 12-1 and the positioning plate 12-3. After positioning pins 125-1 of the lower pressing plate 12-5 pass through mounting holes 124-1 of the funnel-shaped sealing ring 12-4, the funnel-shaped sealing ring 12-4 is fixed between the lower pressing plate 12-5 and the positioning plate 12-3, referring to FIG. 2, FIG. 3 and FIG. 4.

Figure 5:
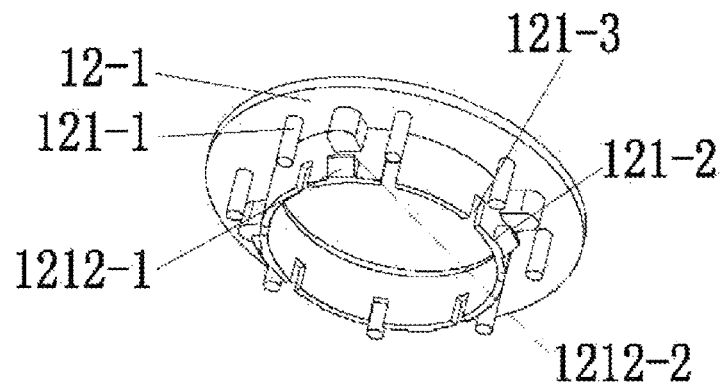
FIG. 5 is a stereostructural schematic diagram of an upper pressing plate of the radial sealing assembly of the present application.
Figures 1, 5:
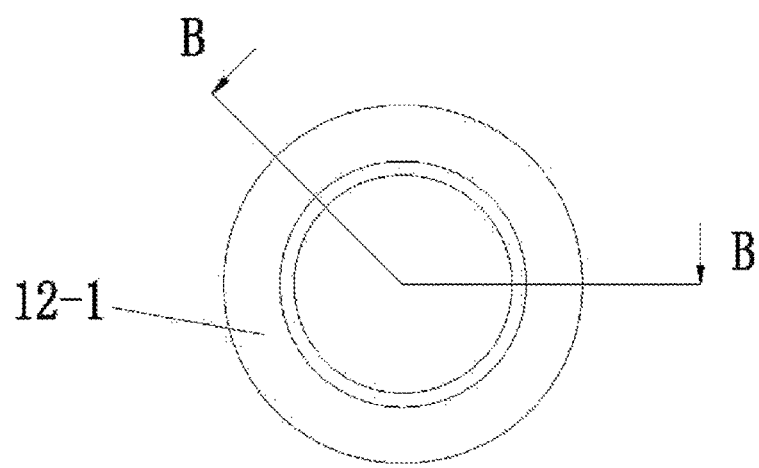
Figures 2, 5:
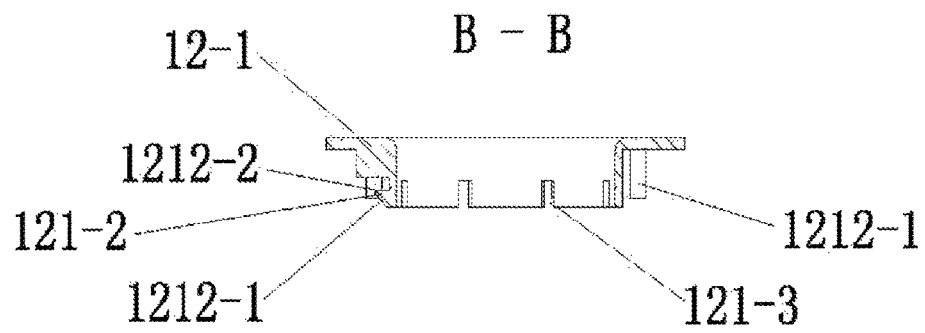

In the present embodiment, the upper pressing plate 12-1 is provided with four convex connecting hooks 121-2 for connection with the positioning plate 12-3, and each convex connecting hook 121-2 is provided with a wedged guiding surface 1212-1 and a positioning working surface 1212-2, referring to FIG. 5 to FIG. 5-2.

Figure 6:
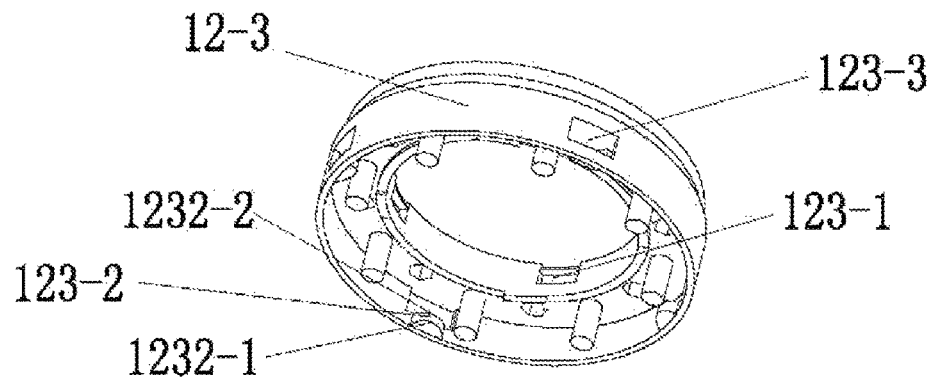
FIG. 6 is a stereostructural schematic diagram of a positioning plate of the radial sealing assembly of the present application.
Figures 1, 6:
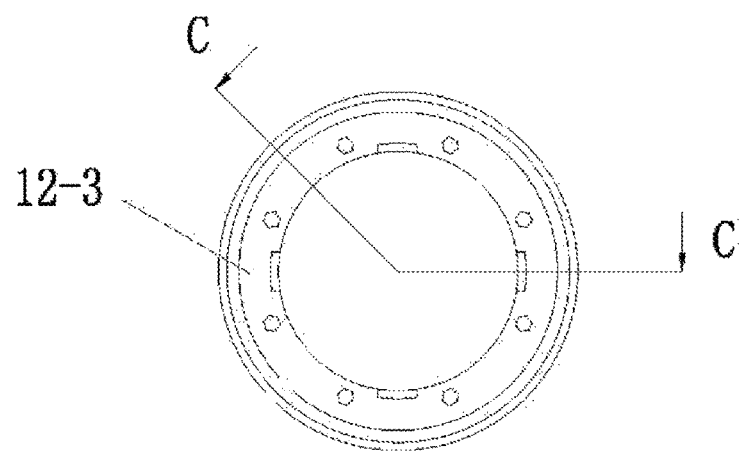
Figures 2, 6:
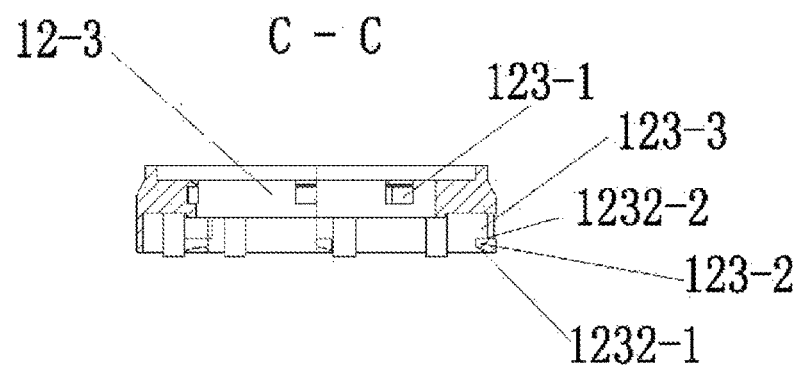

The positioning plate 12-3 is provided with four connecting slots 123-1 for connection with the upper pressing plate 12-1 and four convex connecting hooks 123-2 for connection with the lower pressing plate 12-5; and each convex connecting hook 123-2 is provided with a guiding surface 1232-1 and a positioning working surface 1232-2, referring to FIG. 6 to FIG. 6-2.

Figure 7:
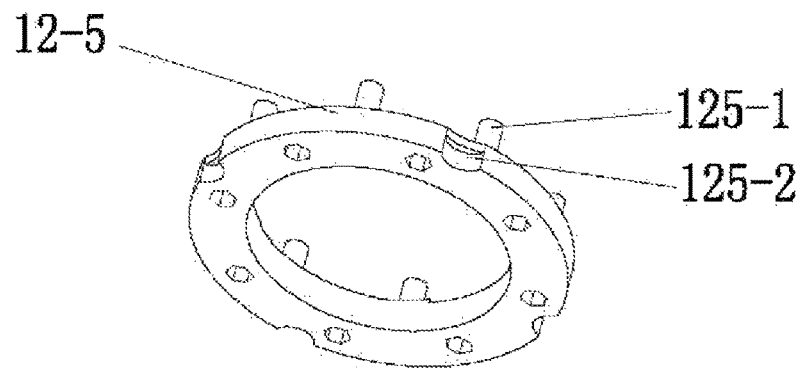
FIG. 7 is a stereostructural schematic diagram of a lower pressing plate of the radial sealing assembly of the present application.
Figures 1, 7:
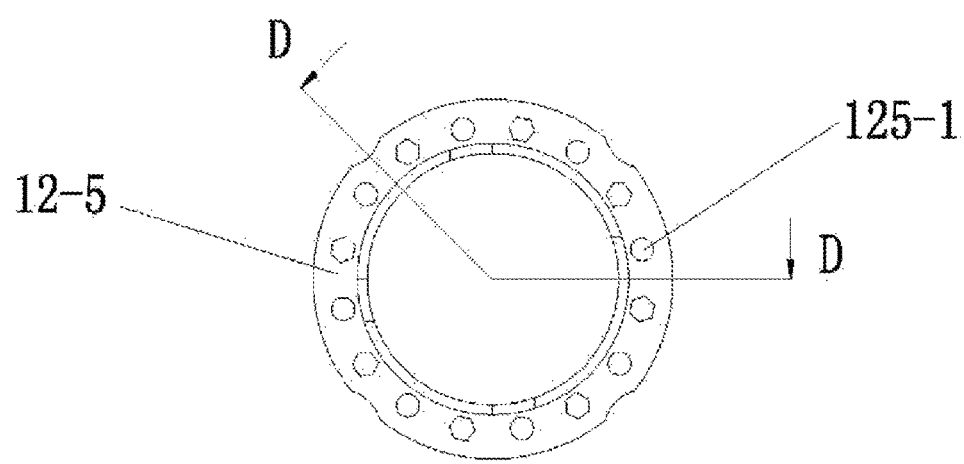
Figures 2, 7:
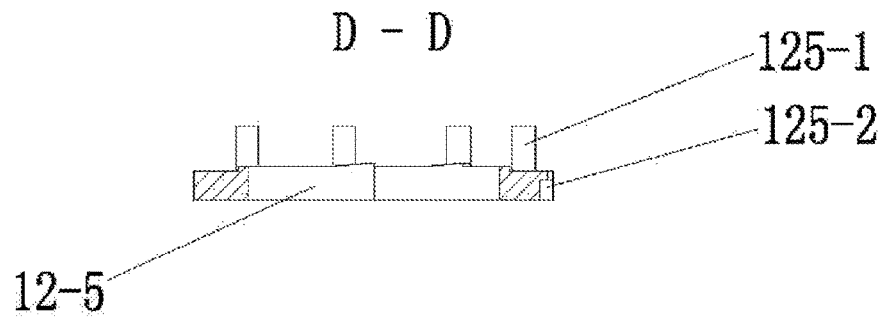
Figure 8:
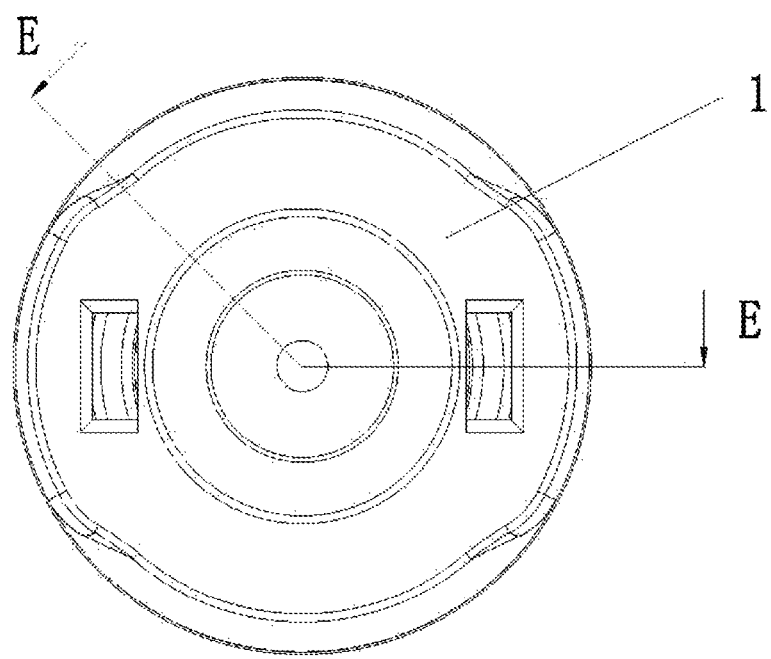
FIG. 8 is a structural schematic diagram of an end sealing piece of the present application.

The lower pressing plate 12-5 is provided with four connecting slots 125-2 for connection with the positioning plate 12-3, referring to FIG. 7 to FIG. 7-2.

Further, the convex connecting hooks 121-2 of the upper pressing plate 12-1 are embedded in the connecting slots 123-1 of the positioning plate 12-3, so that a concave-convex engagement structure is formed to connect the upper pressing plate 12-1 and the positioning plate 12-3 together; and the convex connecting hooks 123-2 of the positioning plate 12-3 are embedded in the connecting slots 125-2 of the lower pressing plate 12-5, so that a concave-convex engagement structure is formed to connect the lower pressing plate 12-5 and the positioning plate 12-3 together, referring to FIG. 2.

Since the convex connecting hooks 121-2 of the upper pressing plate 12-1 are provided with the wedged guiding surfaces 1212-1, during mounting, the convex connecting hooks 121-2 can be conveniently embedded into the connecting slots 123-1 of the positioning plate 12-3. Since the convex connecting hooks 121-2 are also provided with the positioning working surfaces 1212-2, after the convex connecting hooks 121-2 are embedded into the connecting slots 123-1 of the positioning plate 12-3, the positioning working surfaces 1212-2 can play a good positioning role, effectively preventing the convex connecting hooks 121-2 from slipping out of the connecting slots 123-1 of the positioning plate 12-3, and thereby the firmness of connection is ensured, referring to FIG. 2.

Since the convex connecting hooks 123-2 for connection with the lower pressing plate 12-5 on the positioning plate 12-3 are provided with the guiding surfaces 1232-1, during mounting, the convex connecting hooks 123-2 of the positioning plate 12-3 can be conveniently embedded into the connecting slots 125-2 of the lower pressing plate 12-5, so that the concave-convex engagement structure is formed. Since the convex connecting hooks 123-2 for connection with the lower pressing plate 12-5 on the positioning plate 12-3 are also provided with the positioning working surfaces 1232-3, after the convex connecting hooks 123-2 are embedded into the connecting slots 125-2 of the lower pressing plate 12-5, the positioning working surfaces 1232-2 can effectively prevent the convex connecting hooks 123-2 from slipping out of the connecting slots 125-2 of the lower pressing plate 12-5, and thereby the firmness of connection is ensured, referring to FIG. 2.

In the present embodiment, a concave-convex engagement design with four convex connecting hooks and four connecting slots is adopted. Such a four-hole positioning design can ensure the firmness of connection in all directions; on the other hand, the direction of mounting does not need to be deliberately chosen in the mounting process of the four-hole positioning design, and thereby the mounting of the radial sealing assembly 12 is facilitated, referring to FIG. 1 to FIG. 7-2.

Through holes 123-3 are arranged over the convex connecting hooks 123-2 of the positioning plate 12-3. The arrangement of the through holes 123-3 facilitates stripping, and also decreases surrounding force at the convex connecting hooks 123-2, and thereby the convex connecting hooks 123-2 can conveniently slide into the connecting slots 125-2 of the lower pressing plate to form convex-concave engagement during mounting.

Notches 121-3 which facilitate mounting are arranged beside the convex connecting hooks 121-2 of the upper pressing plate 12-1. During assembly, the convex connecting hooks 121-2 can be moderately deformed, and thereby the convex connecting hooks 121-2 can conveniently slide and be embedded into the connecting slots 123-1 of the positioning plate to form concave-convex engagement fixation, referring to FIG. 2, FIG. 5 to FIG. 5-2.

The radial sealing assembly of the present application is convenient to assemble, and the efficiency of production is high; and moreover, the elasticity of sealing ring material can be effectively resisted, connection is firm, and cannot get loose, and air cannot leak out.

Embodiment 2: An End Sealing Piece of the Present Application

The end sealing piece of the present application comprises the radial sealing assembly 12 of claim 1.

In the present embodiment, the end sealing piece 1 comprises the radial sealing assembly 12 described in embodiment 1.

The end sealing piece 1 comprises an upper cover 11, a pressing ring 13, a lower cover 14, and the radial sealing assembly 12 of claim 1, referring to FIG. 8 to FIG. 12-2.

Figure 9:
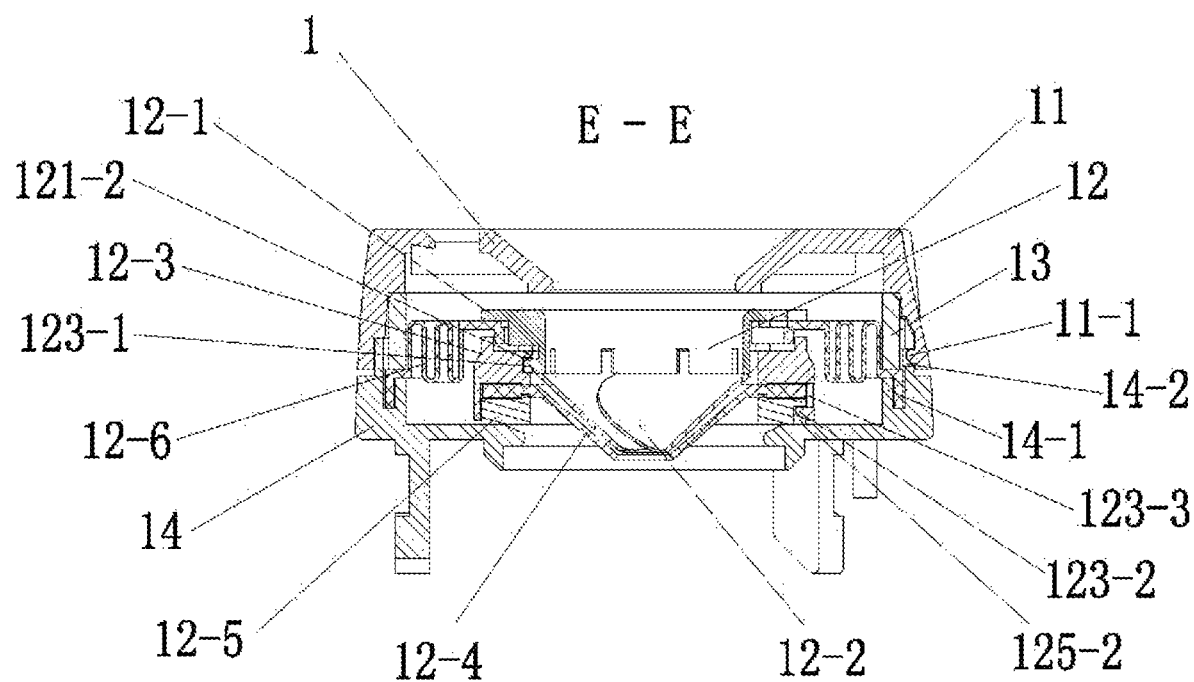
FIG. 9 is an E-E section view of FIG. 8.

The radial sealing assembly 12 and the pressing ring 13 are mounted in a space defined by the upper cover 11 and the lower cover 14; and the outer edge of the corrugated sealing ring 12-6 on the radial sealing assembly 12 is embedded between a sealing rib 14-1 of the lower cover 14 and the pressing ring 13, so that the corrugated sealing ring 12-6 is compressed by the upper cover 11, referring to FIG. 9.

The upper cover 11 and the lower cover 14 are connected together through a concave-convex engagement structure, referring to FIG. 9.

Figure 10:
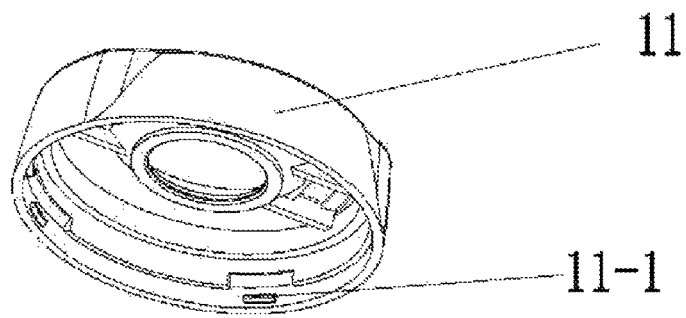
FIG. 10 is a stereostructural schematic diagram of an upper cover of the end sealing piece of the present application.
Figures 1, 10:
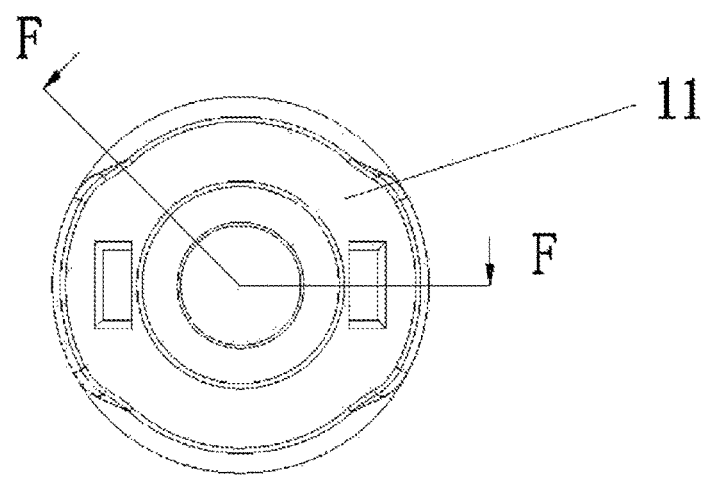
Figures 2, 10:
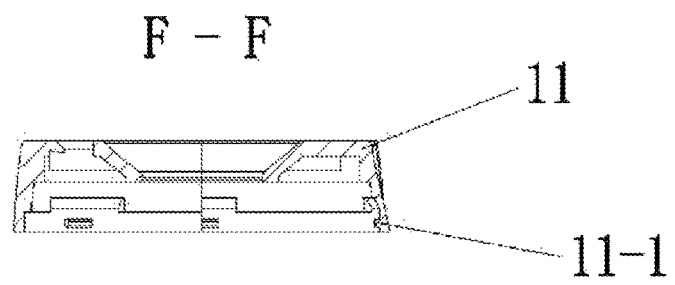
Figure 11:
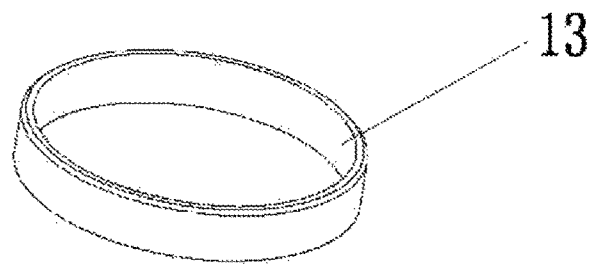
FIG. 11 is a stereostructural schematic diagram of a pressing ring of the end sealing piece of the present application.
Figures 1, 11:
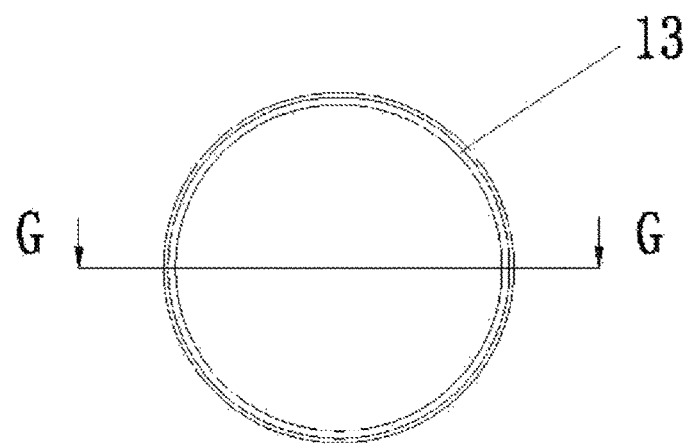
Figures 2, 11:
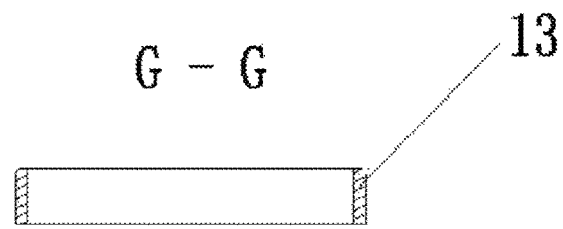
Figure 12:
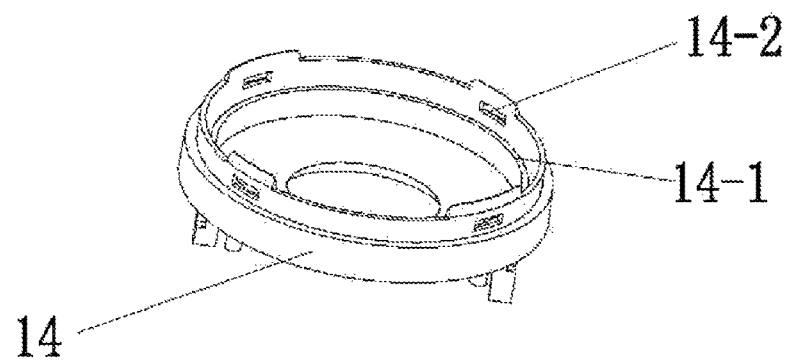
FIG. 12 is a stereostructural schematic diagram of a lower cover of the end sealing piece of the present application.
Figures 1, 12:
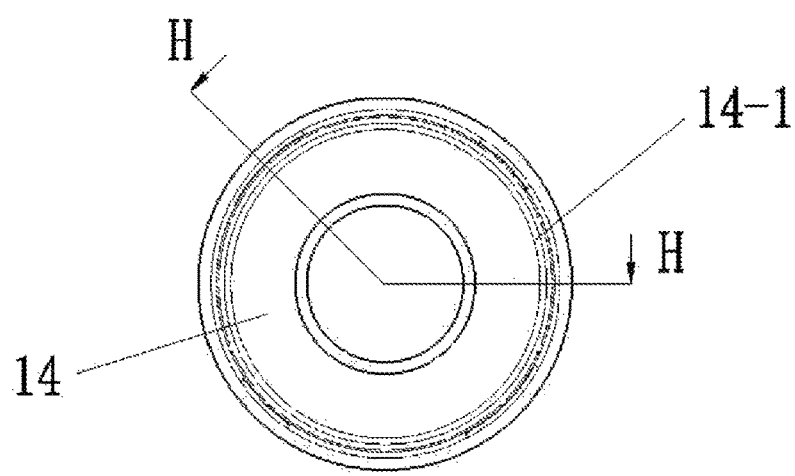
Figures 2, 12:
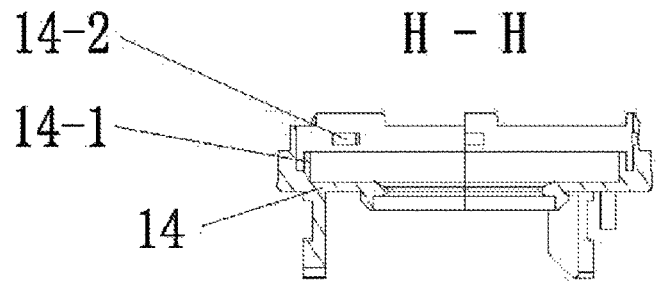

The upper cover 11 is provided with four convex connecting hooks 11-1, referring to FIG. 10 to FIG. 10-2. The lower cover 14 is provided with four connecting slots 14-2, referring to FIG. 12 to FIG. 12-2. The convex connecting hooks 11-1 of the upper cover 11 are embedded in the connecting slots 14-2 of the lower cover 14, so that a concave-convex engagement structure is formed for fixed connection, referring to FIG. 9.

Since the upper cover 11 and the lower cover 14 adopt the concave-convex engagement connection method, mounting is convenient, moreover, the firmness of connection can be effectively ensured, and air leakage can be prevented.

The upper cover 11 and lower cover 14 of the end sealing piece 1 of the present application also can be fixedly connected together by connection methods, such as ultrasonic welding or sticking or interference fit, without departing from the protection scope defined by the present application.

Embodiment 3: A Trocar of the Present Application

The trocar 100 of the present application comprises the radial sealing assembly 12 of claim 1.

Figure 13:
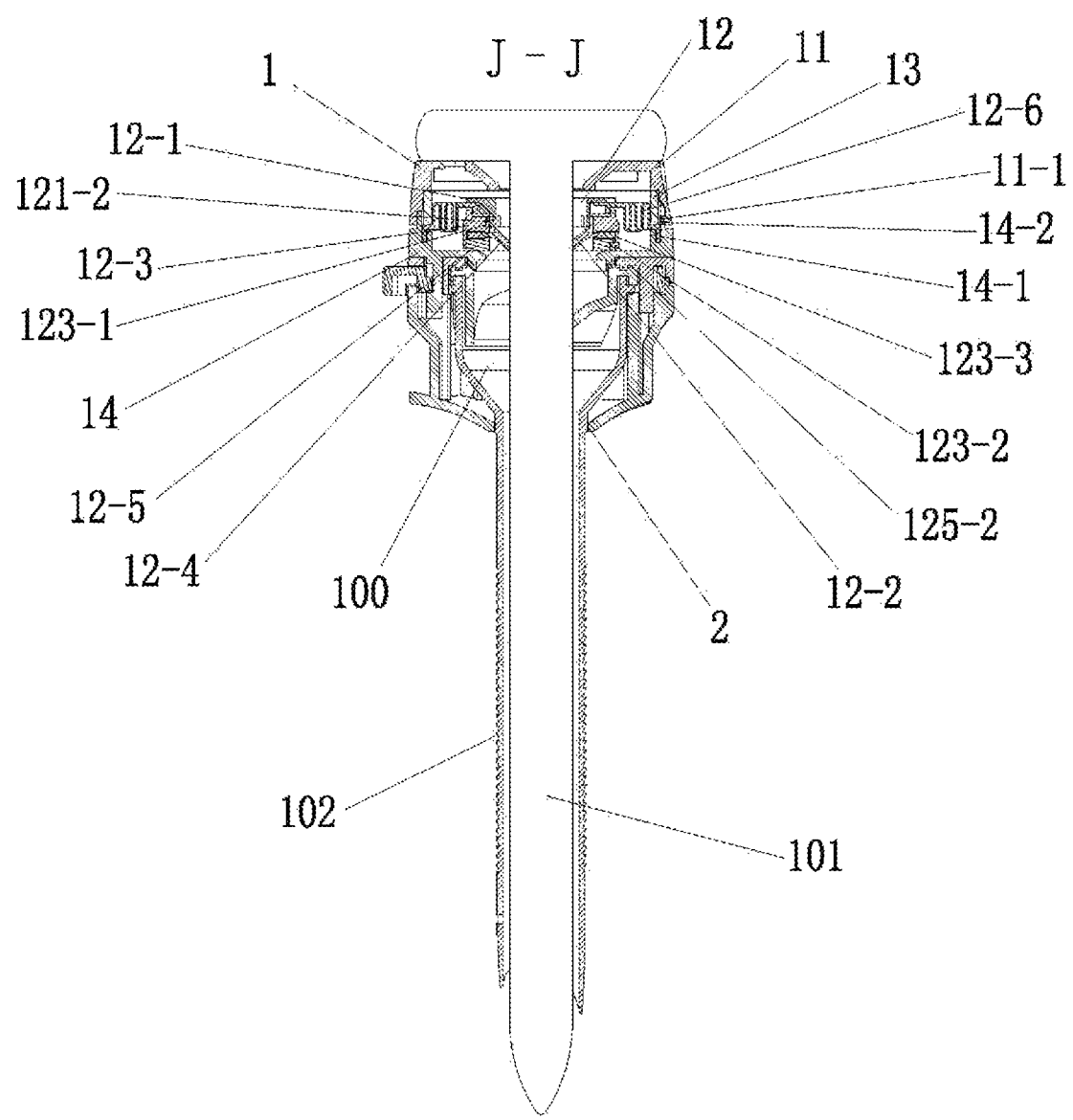
FIG. 13 is a top view of a trocar of the present application.
Figure 14:
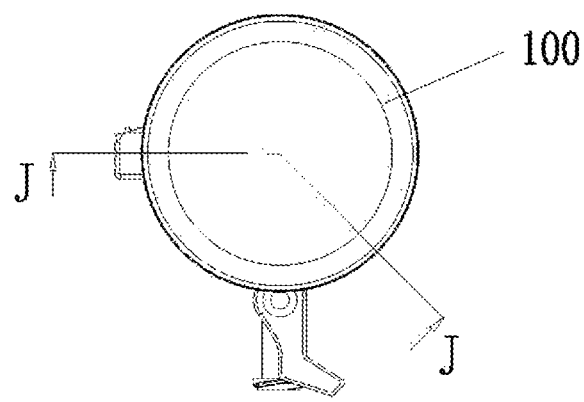
FIG. 14 is a J-J section view of FIG. 13.

Referring to FIG. 13 to FIG. 14, in the present embodiment, the trocar 100 comprises the radial sealing assembly 12 described in embodiment 1. The trocar 100 comprises a trocar rod 101 and a sheath tube 102, and the trocar rod 101 is inserted in the sheath tube 102. The sheath tube 102 comprises and an end sealing piece 1 and a sleeve 2, and the end sealing piece 1 is mounted at the near end of the sleeve 2; the end sealing piece 1 is the end sealing piece 1 of claim 6, and the end sealing piece 1 comprises the radial sealing assembly 12 of claim 1.

The upper cover 11 of the end sealing piece 1 of the trocar 100 is provided with four convex connecting hooks 11-1, and the lower cover 14 is provided with four connecting slots 14-2. The convex connecting hooks 11-1 of the upper cover 11 are embedded in the connecting slots 14-2 of the lower cover 14, so that a concave-convex engagement structure is formed for fixed connection, fixing the upper cover 11 and the lower cover 14 together.

The upper pressing plate 12-1 of the radial sealing assembly 12 of the trocar 100 is provided with four convex connecting hooks 121-2 for connection with the positioning plate 12-3; the positioning plate 12-3 is provided with four connecting slots 123-1 for connection with the upper pressing plate 12-1 and four convex connecting hooks 123-2 for connection with the lower pressing plate 12-5; the lower pressing plate 12-5 is provided with four connecting slots 125-2 for connection with the positioning plate 12-3; the convex connecting hooks 121-2 of the upper pressing plate 12-1 are embedded in the connecting slots 123-1 of the positioning plate 12-3, so that a concave-convex engagement structure is formed to connect the upper pressing plate 12-1 and the positioning plate 12-3 together; and the convex connecting hooks 123-2 of the positioning plate 12-3 are embedded in the connecting slots 125-2 of the lower pressing plate 12-5, so that a concave-convex engagement structure is formed to connect the lower pressing plate 12-5 and the positioning plate 12-3 together.

Since the upper cover 11 and lower cover 14 of the end sealing piece 11 of the trocar 100 of the present application are fixedly connected through the concave-convex engagement structure, the upper pressing plate 12-1 and positioning plate 12-3 of the radial sealing assembly 12 are fixedly connected through the concave-convex engagement structure and the lower pressing plate 12-5 and positioning plate 12-3 of the radial sealing assembly 12 are fixedly connected through the concave-convex engagement structure, the elasticity of sealing ring material can be effectively resisted, connection is firm, air cannot leak out, moreover, assembly is convenient, and the efficiency of production is high.

It should be noted that the structures disclosed and described herein can be substituted by other structures with the same effect, and moreover, the embodiments introduced in the present application are not the only structures implementing the present application. Although the preferred embodiments of the present application have been introduced and described herein, those skilled in the art may all clearly know that these embodiments are merely described as examples, those skilled in the art can make innumerable variations, improvements and substitutes without departing from the present application, and therefore, the protection scope of the present application should be defined according to the spirit and scope of the claims attached to the present application.

What is claimed is:

1. A medical device, comprising:
  a radial sealing assembly, comprising:
    an upper pressing plate;
    a protection sheet;
    a positioning plate;
    a funnel-shaped sealing ring;
    a lower pressing plate; and
    a corrugated sealing ring; wherein:
      positioning pins of the upper pressing plate sequentially pass through mounting holes of the protection sheet and mounting holes of the corrugated sealing ring with the protection sheet and the corrugated sealing ring mounted between the upper pressing plate and the positioning plate, and the protection sheet being mounted between the upper pressing plate and the corrugated sealing ring;
      positioning pins of the lower pressing plate pass through mounting holes of the funnel-shaped sealing ring with the funnel-shaped sealing ring fixed between the lower pressing plate and the positioning plate;
      the upper pressing plate and the positioning plate are connected together by adopting a concave-convex engagement structure; and
      the lower pressing plate and the positioning plate are connected together by adopting a concave-convex engagement structure: and
  a pressing ring; and
  an end sealing piece;
  wherein the radial sealing assembly and the pressing ring are mounted in a space defined by an upper cover and a lower cover of the end sealing piece, wherein an outer edge of the corrugated sealing ring is embedded between a sealing rib of the lower cover and the pressing ring so that the corrugated sealing ring is compressed by the upper cover; and wherein the upper cover and the lower cover are connected together by welding or sticking or interference fit or through a concave-convex engagement structure.

2. The medical device according to claim 1, wherein:
the upper pressing plate is provided with at least two first convex connecting hooks for connection with the positioning plate, and each first convex connecting hook of the upper pressing plate is provided with a wedged guiding surface and a positioning working surface;
the positioning plate is provided with at least two first connecting slots for connection with the upper pressing plate and at least two second convex connecting hooks for connection with the lower pressing plate; and each second convex connecting hook of the positioning plate is provided with a guiding surface and a positioning working surface;
the lower pressing plate is provided with at least two second connecting slots for connection with the positioning plate; and
the at least two first convex connecting hooks of the upper pressing plate are embedded in the at least two first connecting slots of the positioning plate, so that the concave-convex engagement structure is formed to connect the upper pressing plate and the positioning plate together; and the at least two second convex connecting hooks of the positioning plate are embedded in the at least two second connecting slots of the lower pressing plate, so that the concave-convex engagement structure is formed to connect the lower pressing plate and the positioning plate together.

3. The medical device according to claim 2, wherein the upper pressing plate is provided with four first convex connecting hooks for connection with the positioning plate; the positioning plate is provided with four first connecting slots for connection with the upper pressing plate and four second convex connecting hooks for connection with the lower pressing plate; and the lower pressing plate is provided with four second connecting slots for connection with the positioning plate.

4. The medical device according to claim 2, wherein through holes are arranged over the at least two second convex connecting hooks of the positioning plate.

5. The medical device according to claim 1, wherein the upper pressing plate is provided with notches which facilitate mounting the upper pressing plate to the positioning plate.

6. The device according to claim 1, wherein the upper cover is provided with at least two third convex connecting hooks; the lower cover is provided with at least two third connecting slots; and the at least two third convex connecting hooks of the upper cover are embedded in the at least two third connecting slots of the lower cover, so that a concave-convex engagement structure is formed for fixed connection.

7. The medical device according to claim 1, wherein the upper cover is provided with four third convex connecting hooks; and the lower cover is provided with four third connecting slots.

8. The medical device according to claim 1, wherein the end sealing piece is part of a sheath tube of a trocar.

\* \* \* \* \*